(12) United States Patent
Penner et al.

(10) Patent No.: US 11,231,381 B2
(45) Date of Patent: Jan. 25, 2022

(54) HYDROGEN GAS SENSORS BASED ON NANOPARTICLE-DECORATED, PATTERNED CARBON NANOTUBE ROPES

(71) Applicant: The Regents of the University of California, Oakland, CA (US)

(72) Inventors: Reginald M. Penner, Irvine, CA (US); Xiaowei Li, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 1040 days.

(21) Appl. No.: 15/878,134

(22) Filed: Jan. 23, 2018

(65) Prior Publication Data

US 2018/0209926 A1   Jul. 26, 2018

Related U.S. Application Data

(60) Provisional application No. 62/449,548, filed on Jan. 23, 2017.

(51) Int. Cl.
| | | |
|---|---|---|
| *G01N 1/00* | (2006.01) | |
| *G01N 27/12* | (2006.01) | |
| *H01L 51/00* | (2006.01) | |
| *G01N 27/414* | (2006.01) | |
| *G01N 33/00* | (2006.01) | |

(Continued)

(52) U.S. Cl.
CPC ......... *G01N 27/127* (2013.01); *C01B 32/168* (2017.08); *C25D 3/12* (2013.01); *C25D 5/022* (2013.01); *C25D 5/18* (2013.01); *C25D 5/34* (2013.01); *C25D 5/54* (2013.01); *C25D 7/12* (2013.01); *C25D 13/04* (2013.01); *G01N 27/4141* (2013.01); *G01N 33/005* (2013.01); *G03F 7/164* (2013.01); *G03F 7/70* (2013.01); *H01L 51/0006* (2013.01); *H01L 51/0018* (2013.01); *H01L 51/0048* (2013.01); (Continued)

(58) Field of Classification Search
None
See application file for complete search history.

(56) References Cited

U.S. PATENT DOCUMENTS 8,110,883 B2 * 2/2012 Ward ..................... G01J 5/02
                                                              257/428
8,142,984 B2   3/2012 Penner et al.

OTHER PUBLICATIONS

Buttner, W. J.; Post, M. B.; Burgess, R.; Rivkin, C. An Overview of Hydrogen Safety Sensors and Requirements. Int. J. Hydrogen Energy 2011, 36, 2462-2470.

(Continued)

*Primary Examiner* — Jyoti Nagpaul
(74) *Attorney, Agent, or Firm* — Nguyen Tarbet LLC

(57) ABSTRACT

Nanoparticle(NP)-decorated carbon nanotube (CNT) ropes used as sensing elements for hydrogen gas ($H_2$) chemiresistors are described herein. The NP-decorated CNT rope sensors were prepared by dielectrophoretic deposition of a single semiconducting CNT rope followed by the electrode-position of metal nanoparticles to highly disperse said nanoparticles on the CNT surfaces. The rope sensors produced a relative resistance change 20-30 times larger than what was observed at single, pure Pd nanowires. Thus, the rope sensors improved upon all $H_2$ sensing metrics (speed, dynamic range, and limit-of-detection) relative to single Pd nanowires.

6 Claims, 7 Drawing Sheets
(6 of 7 Drawing Sheet(s) Filed in Color)

(51) Int. Cl.

| | |
|---|---|
| *C25D 5/18* | (2006.01) |
| *C25D 5/34* | (2006.01) |
| *C25D 7/12* | (2006.01) |
| *G03F 7/16* | (2006.01) |
| *G03F 7/20* | (2006.01) |
| *C25D 3/12* | (2006.01) |
| *C25D 5/54* | (2006.01) |
| *C25D 5/02* | (2006.01) |
| *C25D 13/04* | (2006.01) |
| *C01B 32/168* | (2017.01) |
| *C25D 3/50* | (2006.01) |

(52) U.S. Cl.
CPC ............ *C01B 2202/02* (2013.01); *C25D 3/50* (2013.01); *G01N 27/4146* (2013.01); *H01L 51/0049* (2013.01)

(56) References Cited

OTHER PUBLICATIONS

Rivkin, C.; Blake, C.; Burgess, R.; Buttner, W. J.; Post, M. B. A National Set of Hydrogen Codes and Standards for the United States. Int. J. Hydrogen Energy 2011, 36, 2736-2741.

Hübert, T.; Boon-Brett, L.; Black, G.; Banach, U. Hydrogen Sensors—a Review. Sensor Actuat. B—Chem. 2011, 157, 329-352.

Korotcenkov, G.; Han, S. D.; Stetter, J. R. Review of Electrochemical Hydrogen Sensors. Chem. Rev. 2009, 109, 1402-1433.

Cheng, P.; Han, P.; Zhao, C.; Zhang, S.; Zhang, X.; Chai, Y. Magnesium Inference Screw Supports Early Graft Incorporation with Inhibition of Graft Degradation in Anterior Cruciate Ligament Reconstruction. Sci. Rep. 2016, 6, 2-12.

Windhagen, H.; Radtke, K.; Weizbauer, A.; Diekmann, J.; Noll, Y.; Kreimeyer, U.; Schavan, R.; Stukenborg-Colsman, C.; Waizy, H. Biodegradable Magnesium-based Screw Clinically Equivalent to Titanium Screw in Hallux Valgus Surgery: Short Term Results of the First Prospective, Randomized, Controlled Clinical Pilot Study. Biomed. Eng. Online 2013, 12, 1.

Hughes, R. C.; Schubert, W. K. Thin-films of Pd/Ni Alloys for Deletion of High Hydrogen Concentrations. J. Appl. Phys. 1992, 71, 542-544.

Li, X. W.; Liu, Y.; Hemminger, J. C.; Penner, R. M. Catalytically Activated Palladium@Platinum Nanowires for Accelerated Hydrogen Gas Detection. ACS Nano 2015, 9, 3215-3225.

Yang, F.; Taggart, D.; Penner, R. Joule Heating a Palladium Nanowire Sensor for Accelerated Response and Recovery to Hydrogen Gas. Small 2010, 6, 1422-1429.

Yang, F.; Kung, S.-C.; Cheng, M.; Hemminger, J. C.; Penner, R. M. Smaller is Faster and More Sensitive: The Effect of Wire Size on the Detection of Hydrogen by Single Palladium Nanowires. ACS Nano 2010, 4, 5233-5244.

Yang, F.; Taggart, D. K.; Penner, R. M. Fast, Sensitive Hydrogen Gas Detection Using Single Palladium Nanowires That Resist Fracture. Nano Lett. 2009, 9, 2177-2182.

Zeng, X.; Latimer, M.; Xiao, Z.; Panuganti, S.; Welp, U.; Kwok, W.; Xu, T. Hydrogen Gas Sensing with Networks of Ultrasmall Palladium Nanowires Formed on Filtration Membranes. Nano Lett. 2010, 11, 262-268.

Offermans, P.; Tong, H. D.; Van Rijn, C. J. M.; Merken, P.; Brongersma, S. H.; Crego-Calama, M. Ultralow-power Hydrogen Sensing with Single Palladium Nanowires. Appl. Phys. Lett. 2009, 94, 223110.

Collins, P. G.; Bradley, K.; Ishigami, M.; Zettl, A. Extreme Oxygen Sensitivity of Electronic Properties of Carbon Nanotubes. Science 2000, 287, 1801-1804.

Liu, R.; Ding, H.; Lin, J.; Shen, F.; Cui, Z.; Zhang, T. Fabrication of Platinum-decorated Singlewalled Carbon Nanotube Based Hydrogen Sensors by Aerosol Jet Printing. Nanotechnology 2012, 23, 505301.

Kumar, M. K.; Ramaprabhu, S. Nanostructured Pt Functionlized Multiwalled Carbon Nanotub Based Hydrogen Sensor. J. Phys. Chem. B 2006, 110, 11291-11298.

Kaniyoor, A.; Jafri, R. I.; Arockiadoss, T.; Ramaprabhu, S. Nanostructured Pt Decorated Graphene and Multi-walled Carbon Nanotube Based Room Temperature Hydrogen Gas Sensor. Nanoscale 2009, 1, 382-386.

Khalap, V. R.; Sheps, T.; Kane, A. A.; Collins, P. G. Hydrogen Sensing and Sensitivity of Palladium-decorated Single-walled Carbon Nanotubes with Defects. Nano Lett. 2010, 10, 896-901.

Wang, J.; Singh, B.; Park, J.-H.; Rathi, S.; Lee, I.-Y.; Maeng, S.; Joh, H.-I.; Lee, C.-H.; Kim, G.-H. Dielectrophoresis of Graphene Oxide Nanostructures for Hydrogen Gas Sensor at Room Temperature. Sensor Actuat. B—Chem. 2014, 194, 296-302.

Chung, M. G.; Kim, D. H.; Seo, D. K.; Kim, T.; Im, H. U.; Lee, H. M.; Yoo, J. B.; Hong, S. H.; Kang, T. J.; Kim, Y. H. Flexible Hydrogen Sensors Using Graphene with Palladium Nanoparticle Decoration. Sensor Actuat. B—Chem. 2012, 169, 387-392.

Zhang, M. L.; Brooks, L. L.; Chartuprayoon, N.; Bosze, W.; Choa, Y. H.; Myung, N. V. Palladium/Single-walled Carbon Nanotube Back-to-back Schottky Contact-based Hydrogen Sensors and Their Sensing Mechanism. ACS Appl. Mater. Interfaces 2014, 6, 319-326.

Choi, B.; Lee, D.; Ahn, J. H.; Yoon, J.; Lee, J.; Jeon, M.; Kim, D. M.; Kim, D. H.; Park, I.; Choi, Y. K. et al. Investigation of Optimal Hydrogen Sensing Performance in Semiconducting Carbon Nanotube Network Transistors with Palladium Electrodes. Appl. Phys. Lett. 2015, 107, DOI: 10.1063/1.4935610.

Dhall, S.; Jaggi, N.; Nathawat, R. Functionalized Multiwalled Carbon Nanotubes Based Hydrogen Gas Sensor. Sensor Actuat. A—Phys. 2013, 201, 321-327.

Lee, J.-H.; Kang, W.-S.; Najeeb, C. K.; Choi, B.-S.; Choi, S.-W.; Lee, H. J.; Lee, S. S.; Kim, J.-H. A Hydrogen Gas Sensor Using Single-walled Carbon Nanotube Langmuir-Blodgett Films Decorated with Palladium Nanoparticles. Sensor Actuat. B—Chem. 2013, 188, 169-175.

Lin, T. C.; Huang, B. R. Palladium Nanoparticles Modified Carbon Nanotube/Nickel Composite Rods (Pd/CNT/Ni) for Hydrogen Sensing. Sensor Actuat. B—Chem. 2012, 162, 108-113.

Pohl, H. A. Theoritical Aspects of Dielectrophoretic Deposition and Separation of Particles. Journal of The Electrochemical Society 1968, 115, 155C-161C.

Xiang, C.; Yang, Y.; Penner, R. M. Cheating the Diffraction Limit: Electrodeposited Nanowires Patterned by Photolithography. Chem. Comm. 2009, 859-873.

Xiang, C.; Kung, S. C.; Taggart, D.; Yang, F.; Thompson, M. A.; Güell, A. G.; Yang, Y.; Penner, R. M. Lithographically Patterned Nanowire Electrodeposition: A Method for Patterning Electrically Continuous Metal Nanowires on Dielectrics. ACS Nano 2008, 2, 1939-1949.

Menke, E. J.; Thompson, M. A.; Xiang, C.; Yang, L. C.; Penner, R. M. Lithographically Patterned Nanowire Electrodeposition. Nat. Mater. 2006, 5, 914-919.

Krupke, R.; Hennrich, F.; Weber, H.; Kappes, M.; V. Löhneysen, H. Simultaneous Deposition of Metallic Bundles of Single-walled Carbon Nanotubes Using AC-dielectrophoresis. Nano Lett. 2003, 3, 1019-1023.

Suehiro, J.; Zhou, G.; Hara, M. Fabrication of a Carbon Nanotube-based Gas Sensor Using Dielectrophoresis and Its Application for Ammonia Detection by Impedance Spectroscopy. J. Phys. D: Appl. Phys. 2003, 36, L109.

Shekhar, S.; Stokes, P.; Khondaker, S. I. Ultrahigh Density Alignment of Carbon Nanotube Arrays by Dielectrophoresis. ACS Nano 2011, 5, 1739-1746.

Stokes, P.; Khondaker, S. I. High Quality Solution Processed Carbon Nanotube Transistors Assembled by Dielectrophoresis. Appl. Phys. Lett. 2010, 96, 083110.

Monica, A.; Papadakis, S.; Osiander, R.; Paranjape, M. Wafer-level Assembly of Carbon Nanotube Networks Using Dielectrophoresis. Nanotechnology 2008, 19, 085303.

Fan, Y.; Goldsmith, B. R.; Collins, P. G. Identifying and Counting Point Defects in Carbon Nanotubes. Nat. Mater. 2005, 4, 906-911.

(56) References Cited

OTHER PUBLICATIONS

Lee, J. S.; Oh, J.; Jun, J.; Jang, J. Wireless Hydrogen Smart Sensor Based on Pt/Graphene-Immobilized Radio-Frequency Identification Tag. ACS Nano 2015, 9, 7783-7790.
Russo, P. A.; Donato, N.; Leonardi, S. G.; Baek, S.; Conte, D. E.; Neri, G.; Pinna, N. Room-Temperature Hydrogen Sensing with Heteronanostructures Based on Reduced Graphene Oxide and Tin Oxide. Angew. Chem. Int. Ed. Engl. 2012, 51, 11053-11057.
Lim, Y.; Lee, Y.; Heo, J.-I.; Shin, H. Highly Sensitive Hydrogen Gas Sensor Based on a Suspended Palladium/Carbon Nanowire Fabricated via Batch Microfabrication Processes. Sensor Actual. B—Chem. 2015, 210, 218-224.
Randeniya, L. K.; Martin, P. J.; Bendavid, A. Detection of Hydrogen Using Multi-walled Carbon-nanotube Yarns Coated with Nanocrystalline Pd and Pd/Pt Layered Structures. Carbon 2012, 50, 1786-1792.
Rumiche, F.; Wang, H. H.; Indacochea, J. E. Development of a Fast-Response/High-sensitivity Double Wall Carbon Nanotube Nanostructured Hydrogen Sensor. Sensor Actuat. B—Chem. 2012, 163, 97-106.
Sun, Y. G.; Wang, H. H. High-performance, Flexible Hydrogen Sensors That Use Carbon Nanotubes Decorated with Palladium Nanoparticles. Adv. Mater. 2007, 19, 2818-2823.
Mubeen, S.; Zhang, T.; Yoo, B.; Deshusses, M. A.; Myung, N. V. Palladium Nanoparticles Decorated Single-walled Carbon Nanotube Hydrogen Sensor. J. Phys. Chem. C 2007, 111, 6321-6327.
Yang, F.; Donavan, K. C.; Kung, S.-C.; Penner, R. M. The Surface Scattering-based Detection of Hydrogen in Air Using a Platinum Nanowire. Nano Lett. 2012, 12, 2924-2930.

\* cited by examiner

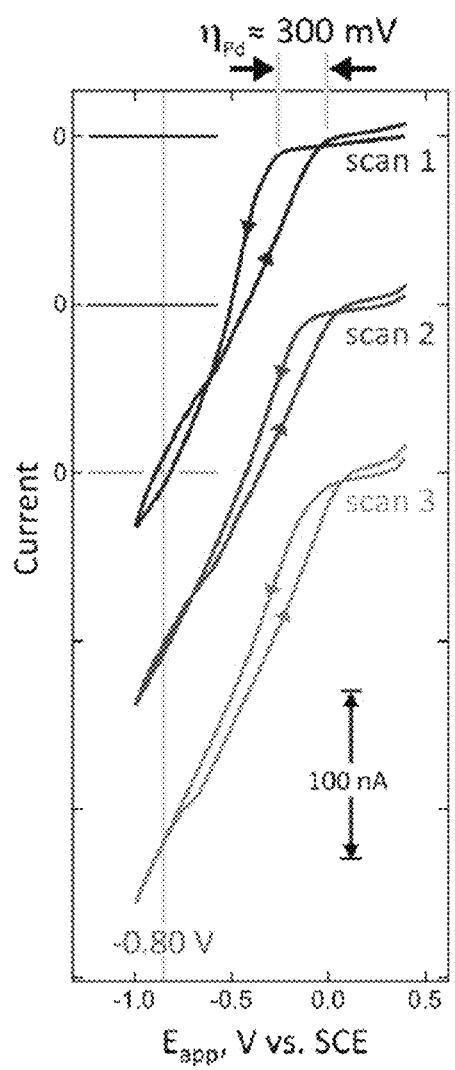
FIG. 3A
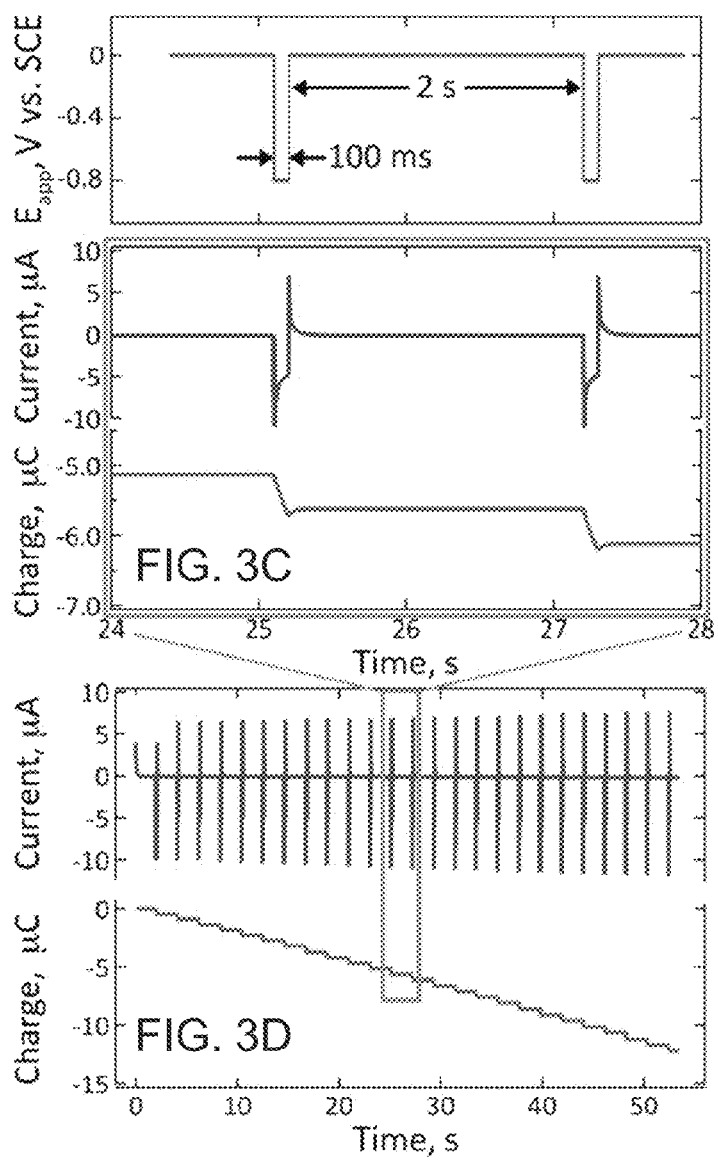
FIG. 3B
FIG. 3C
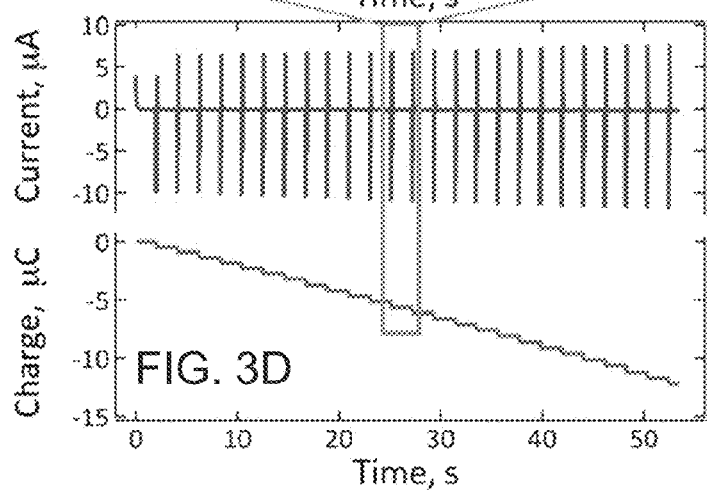
FIG. 3D

HYDROGEN GAS SENSORS BASED ON NANOPARTICLE-DECORATED, PATTERNED CARBON NANOTUBE ROPES

CROSS REFERENCE

This application claims priority to U.S. Patent Application No. 62/449,548 filed Jan. 23, 2017, the specification(s) of which is/are incorporated herein in their entirety by reference.

GOVERNMENT SUPPORT

This invention was made with government support under Grant No. CHE-1306928 awarded by NSF. The government has certain rights in the invention.

FIELD OF THE INVENTION

The present invention relates to nano-electronic devices and fabrication thereof using patterned carbon nanotube ropes, in particular, to hydrogen gas sensors with rapid and ultrasensitive performance based on said carbon nanotube ropes.

BACKGROUND OF THE INVENTION

Hydrogen is the lightest element, and hydrogen gas (dihydrogen or molecular hydrogen, $H_2$) is highly flammable and can be ignited in air at a wide concentration range between 4 vol % and 75 vol %. Additionally, this gas is colorless and odorless; thus, sensors that are capable of detecting hydrogen ($H_2$) gas in air are important and necessary for the detection of leaked hydrogen, for control of chemical processes in industry, and for investigations of physiological processes among other applications. The Department of Energy raised the requirements for evaluating the key parameters of hydrogen safety sensors; for example, the sensors should have a fast response/recovery (1 min for 1 vol % hydrogen) and a wide dynamic sensing range (0.1 vol % to 4 vol %). Previously developed hydrogen sensors that show slow response or narrow sensing range cannot meet such requirements.

Chemiresistors are amongst the simplest chemical sensor architectures. The first chemiresistor for $H_2$ gas consisted of an evaporated palladium-nickel alloy film resistor. These simple devices produced a rapid response to $H_2$ exposure (at 4%) of several seconds but were not able to detect hydrogen in air at low concentrations, below 0.1%. Nanowire chemiresistors accelerate response and recovery to $H_2$, but the limit-of-detection for $H_2$ in air ($LOD_{H2} \approx 0.05\%$ at RT) was only slighted improved compared with Pd—Ni film chemiresistors ($LOD_{H2} \approx 0.1\%$).

Since single walled carbon nanotubes (SWCNTs) were observed to be strongly affected by ambient gas composition, carbon nanotubes (CNTs) have been studied as components of chemiresistive sensors. For instance, CNTs decorated with Pd and Pt nanoparticles were evaluated as $H_2$ sensors. Also, the response to $H_2$ of graphene-supported with Pd and Pt nanoparticles has also been studied and metrics for response/recovery speed and $LOD_{H2}$ were similar to those obtained for SWCNTs and, as in the case of SWCNTs, were also highly variable. A third category of sensors exploit palladium Schottky contacts, but no dispersed Pd or Pt particles, to enable $H_2$ detection at either CNTs or graphene. An important problem with both graphene and CNT-based sensors is that exposure to $H_2$ did not yield a steady-state, time invariant change in electrical resistance. Instead, an increasing resistance is observed during $H_2$ exposures, sometimes lasting minutes, independent of the $H_2$ concentration. For many graphene and CNT-based devices, the sensor resistance either does not stabilize at all or it fails to do so in a useful time scale. Pd nanowires, in contrast, do not exhibit this problem.

To summarize, with a few exceptions, palladium nanowires are capable of functioning as chemiresistors for $H_2$ that respond and recover rapidly in air but are relatively insensitive. Pd-decorated SWCNTs and graphene can be highly sensitive but are usually slow and even failing, in many cases, to produce a time-invariant resistance change. Hence, sensors that have rapid and sensitive detection of leaked hydrogen gas in air still remains technologically challenging.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide for hydrogen gas safety sensors that exhibit a wider detectable hydrogen concentrations range, reduced power consumption, and more rapid sensing behaviors, as specified in the independent claims. Embodiments of the invention are given in the dependent claims. Embodiments of the present invention can be freely combined with each other if they are not mutually exclusive.

In some aspects, the present invention features a hydrogen safety sensor based on patterned carbon nanotube ropes decorated with metal nanoparticles. These sensors exhibit a very wide detection range with observed sensing signals for the hydrogen gas concentrated ranging from 10 ppm (0.001 vol %) to 4 vol %. Further still, these hydrogen gas safety sensors demonstrated rapid response and recovery behaviors to all hydrogen exposures. The sensing element, which is the interface barrier between nanoparticles and carbon nanotubes, can amplify the sensing signal dramatically as compared to Pd nanowires. The carbon nanotube ropes can be utilized for a wide range of applications, including chemical/biological sensors, strain/pressure sensors, microelectronics, energy storage and so forth.

According to exemplary embodiments, the $H_2$ sensor may comprise a supporting substrate, a carbon nanotube (CNT) rope electrodeposited onto the supporting substrate, at least two metal electrodes disposed on the CNT rope with a portion of the CNT rope disposed in-between the two metal electrodes, and metal nanoparticles (NPs) electrodeposited onto the portion of the CNT rope that is disposed between the two metal electrodes. In some embodiments, the metal NPs may have a mean particle diameter of about 4-10 nm. Without wishing to limit the invention to a particular theory or mechanism, it is believed that the mean particle diameter size advantageously allows for the $H_2$ sensor to detect $H_2$ in air at an $H_2$ concentration of at least 10 ppm.

In yet other aspects, the present invention also features a method of producing the $H_2$ gas sensor. The method may comprise electrodepositing a carbon nanotube (CNT) rope on a supporting substrate, electrodepositing at least two metal electrodes on the CNT rope disposed on the supporting substrate such that a portion of the CNT rope is disposed in-between the two metal electrodes, depositing a photoresist layer on the two metal electrodes, the CNT rope, and the supporting substrate, and lithographically patterning the photoresist layer to form a window through the photoresist layer, thus exposing and isolating a portion of the CNT rope disposed between the two metal electrodes. The method may further comprise electrodepositing, via a pulse electrodeposition process, metal NPs onto the CNT rope that is exposed and isolated between the two metal electrodes, thus forming the $H_2$ sensor comprising a metal NP-decorated CNT rope.

One of the unique and inventive technical features of the present invention is the pulse electrodeposition process comprising applying about 50-400 voltage pulses, each pulse having an applied potential of about −0.8 V vs. SCE and a pulse duration of about 0.1-0.5 second and being separated by about 1-2 second wait times. This process results in the formation of a high density of metal nanoparticles decorating the CNT rope. For instance, in some embodiments, the present invention has the ability to manufacture sensors featuring CNT rope decorated with millions of sub-6 nm diameter Pd nanoparticles, which is significantly easier to produce than the single Pd nanoparticle on a single carbon nanotube as taught by Khalap et al. (Khalap, V. R.; Sheps, T.; Kane, A. A.; Collins, P. G. Hydrogen Sensing and Sensitivity of Palladium-decorated Single-walled Carbon Nanotubes with Defects. Nano Lett. 2010, 10, 896-901).

Without wishing to limit the invention to any theory or mechanism, the technical feature advantageously provides carbon nanotube based sensors that: i) have low power consumption in micro-watts range, ii) economically use precious materials since tiny amount of carbon nanotubes and rare metal are needed, and iii) have flexibility and resistivity to mechanical and thermal shocks since carbon nanotube based sensors can be stretched, twisted and bent, particularly considering the application of making wearable and portable devices. None of the presently known prior references or work has the unique inventive technical feature of the present invention.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 2A shows current versus time for the dielectrophoretic deposition of CNT ropes at an LPNE-patterned template induced by a train of +20 V×0.10 s pulses separated in time by 1.0 s. FIG. 2B shows a scanning electron micrograph (SEM) of an array of CNT ropes on glass patterned at 20 µm pitch using LPNE. FIG. 2C shows an SEM image of loops of CNT rope patterned at 100 µm pitch using LPNE. FIG. 2D is a higher magnification SEM image of a section of CNT rope 1.0-1.5 µm in width. FIG. 2E shows a Pd-CNT rope H2 sensor comprising a single CNT rope decorated with Pd nanoparticles (not visible in this image) and evaporated gold electrical contacts.

FIGS. 3A-3D show data for electrodeposition of Pd NPs onto CNT ropes. FIG. 3A shows cyclic voltammograms at 20 mV/s in aqueous 0.2 mM PdCl2, 0.22 mM EDTA, 0.1 M KCl showing reduction of $Pd^{2+}$ and concurrent H2 evolution. FIG. 3B show an example of a pulse program for applying a train of potential pulses of −0.80 V vs. SCE to electrodeposit Pd nanoparticles onto a single CNT rope. FIG. 3C shows current (blue trace) and charge (green trace) versus time for two deposition pulses illustrating the build-up of cathodic charge corresponding to both Pd reduction ($Pd^{2+}+2e^-\rightarrow Pd^0$) and $H_3O^+$ reduction ($H_3O^++2e^- \rightarrow H_2+OH^-$).

FIG. 4A shows a low magnification TEM image of a CNT rope after the deposition of palladium nanoparticles ($Q_{Pd}$=42° C.). Palladium nanoparticles are distributed across this entire image, with some of the largest seen as dark spots in the lower right corner of this image. FIG. 4B shows a high resolution TEM image of one of the nanoparticles in the blue circles that highlight approximately 40 Pd nanoparticles present in the region shown in the inset, which shows a higher magnification view of the region shown in FIG. 4A. FIG. 4C shows histograms of Pd nanoparticle diameters obtained from TEM analysis of either 2 or 3 sensors prepared using the indicated $Q_{Pd}$

FIG. 6A shows $\Delta R/R_0$, the relative resistance change, versus [$H_2$] in air for five sensors, as indicated. Parameters for the Pd-CNT rope $H_2$ sensors are later summarized in Table 2. $\Delta R/R_0$ increases monotonically with Pd loading, and the mean Pd particle diameter. FIG. 6B shows a response time versus [$H_2$] in air, and FIG. 6C shows a recovery time versus [$H_2$] in air for the same five sensors described in FIG. 6A.

DESCRIPTION OF PREFERRED EMBODIMENTS

Figure 1:
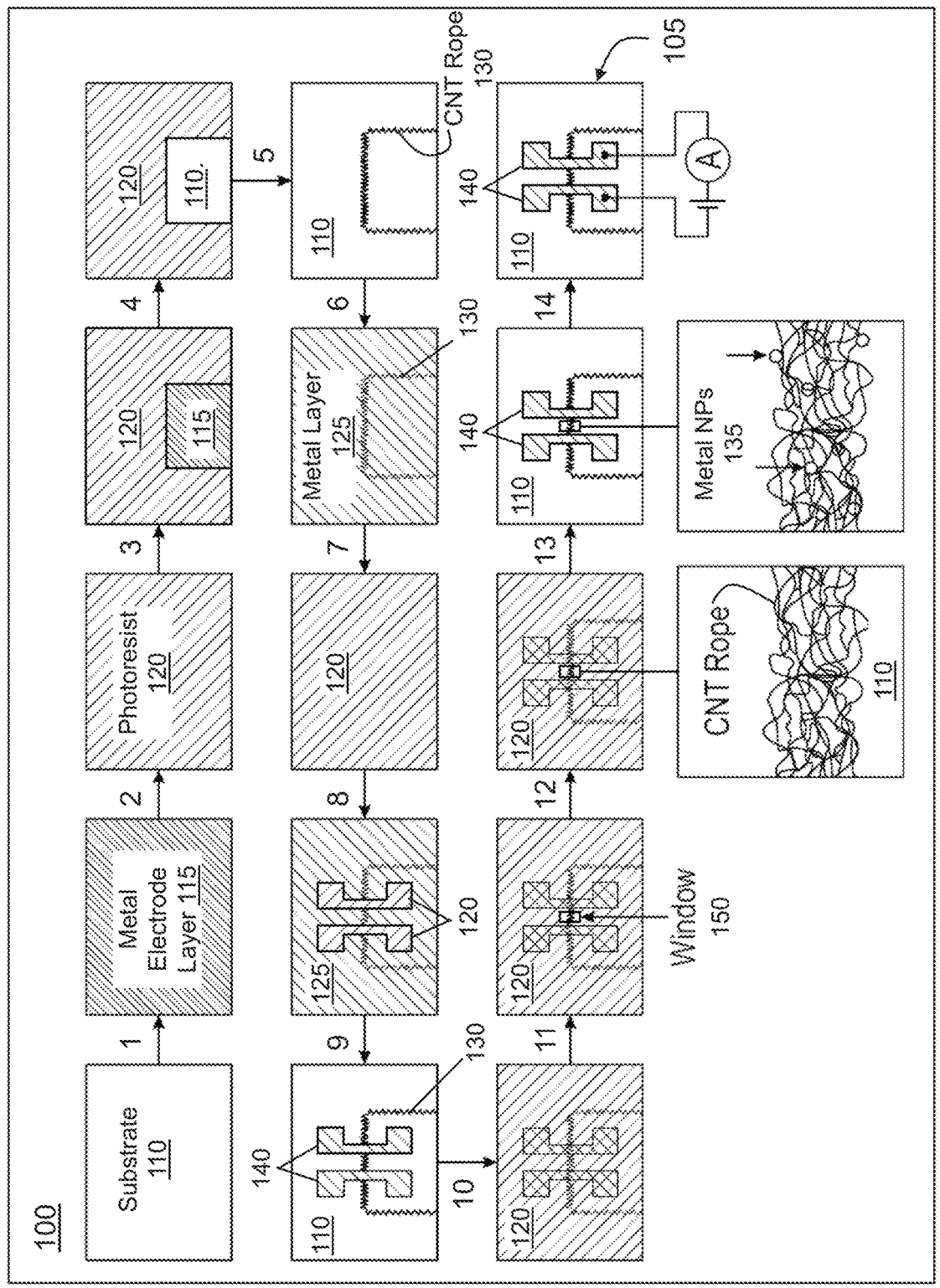
FIG. 1 shows a non-limiting embodiment of a process flow diagram for fabrication of a CNT@PdNP $H_2$ sensor.

Following is a list of elements corresponding to a particular element referred to herein:
105 $H_2$ sensor
110 substrate
115 metal electrode layer
120 photoresist
125 metal layer
130 carbon nanotube rope
135 metal nanoparticle
140 metal electrodes
150 window Referring now to FIG. 1, in some embodiments, the present invention features a method (100) of producing a metal nanoparticle (NP)-decorated carbon nanotube (CNT)

rope. The method (100) may comprise electrodepositing a CNT rope (130) on a supporting substrate (110), followed by electrodepositing at least two metal electrodes (140) on the CNT rope (130) disposed on the supporting substrate (110) such that a portion of the CNT rope is disposed in-between the two metal electrodes (140). In other embodiments, the method may further comprise depositing a photoresist layer (120) on the two metal electrodes (140), CNT rope (130), and the supporting substrate (110), and lithographically patterning the photoresist layer (120) to form a window (150) through the photoresist layer (120), thus exposing and isolating a portion of the CNT rope (130) disposed between the two metal electrodes (140). Metal nanoparticles (135) are then electrodeposited onto the CNT rope (130) exposed and isolated between the two metal electrodes (140), thus forming the metal NP-decorated CNT rope. The metal NPs (135) may comprise palladium, platinum, nickel, gold, or a combination thereof.

In some embodiments, the electrodeposition of metal NPs may comprise a pulse electrodeposition process in which about 50-400 voltage pulses is applied, with each pulse having an applied potential of about −0.8 V vs. a saturated calomel electrode (SCE) and a pulse duration of about 0.1-0.5 second and being separated by about 1-2 second wait times. Without wishing to limit the invention to a particular theory or mechanism, the pulse electrodeposition process can form metal NPs (135) having a mean particle diameter of about 4-10 nm. The process can also maximize a density of metal NPs formed on the exposed and isolated CNT rope (130).

In other embodiments, the step of electrodepositing the CNT rope (130) on the supporting substrate (110) may comprise thermally evaporating a metal electrode layer (115) on the supporting substrate (110), depositing a photoresist layer (120) on the metal electrode layer (115), lithographically patterning the photoresist layer (120) to expose a portion of the metal electrode layer (115), and etching away the exposed metal electrode layer (115) to produce a horizontal trench beneath the photoresist layer (120). In some embodiments, the metal electrode layer (115) may be comprised of nickel. In some embodiments, the edges of the metal electrode layer within the horizontal trench can act as a working electrode. In other embodiments, a height of the horizontal trench may be equal to a thickness of the metal electrode layer.

Continuing with the process of electrodepositing the CNT rope (130), single walled carbon nanotubes (SWCNTs) may be dielectrophoretically deposited by applying of a series of voltage pulses to generate the CNT rope (130) within the horizontal trench. In some embodiments, the series of voltage pulses comprises about 50-100 voltages pulses, each pulse having an amplitude of about 20 V applied for a duration of about 0.1-0.5 second, at a rate of one pulse for every 1-2 seconds. Lastly, the remaining photoresist layer (120) is removed and the remaining metal electrode layer (115) is etched away, thus producing the CNT rope (130) adhered to the supporting substrate (110).

In some embodiments, the step of electrodepositing at least two metal electrodes (140) may comprise thermally evaporating at least one metal layer (125) onto the CNT rope (130) disposed on the supporting substrate (110), depositing a photoresist layer (120) on the metal layer (125), and lithographically patterning the photoresist layer (120) to form at least two electrode patterns on the metal layer (125) with a portion of the CNT rope disposed between the two electrode patterns. In some embodiments, the metal layer (125) may comprise copper, silver, or gold. In other embodiments, the metal layer (125) may further comprise an adhesive interlayer, such as chromium. Continuing with the step of electrodepositing the metal electrodes, uncovered portions of the metal layer (125) are etched away, and the electrode patterns of the remaining photoresist layer (120) are stripped from the remaining metal layer (125), thus forming the at least two metal electrodes (140) with the portion of the CNT rope disposed in-between. As used herein, electrodeposition of the metal electrodes (140) on the CNT rope (130) is intended to operatively connect the metal electrodes (140) to the CNT rope. In some embodiments, as shown in step 14 of FIG. 1, only a portion of each metal electrode (140) is required to be in direct contact with the CNT rope, provided that said contact enables a working electrical connection.

In preferred embodiments, the metal NP-decorated carbon CNT ropes may be used as hydrogen gas ($H_2$) sensors (105) for sensing $H_2$ gas in air. For example, in one embodiment, the present invention may feature an $H_2$ sensor comprising a supporting substrate (110), a carbon nanotube (CNT) rope (130) electrodeposited onto the supporting substrate (110), at least two metal electrodes (140) disposed on the CNT rope (130) with a portion of the CNT rope (130) disposed in-between the two metal electrodes (140), and metal nanoparticles (NPs) (135) electrodeposited onto the portion of the CNT rope (130) that is disposed between the two metal electrodes (140). In some embodiments, the metal NPs (135) may have a mean particle diameter of about 4-10 nm. Without wishing to limit the invention to a particular theory or mechanism, it is believed that the mean particle diameter size advantageously allows for the $H_2$ sensor (105) to detect $H_2$ in air at an $H_2$ concentration of at least 10 ppm. In some embodiments, the metal NPs (135) may comprise palladium, platinum, nickel, gold, or a combination thereof. In other embodiments, the metal electrodes (140) may be comprised of copper, silver, or gold. In further embodiments, the metal electrodes (140) may also include an adhesive interlayer, such as a chromium adhesive interlayer.

According to some embodiments, the present invention also features a method of producing $H_2$ gas sensor (105). In one aspect, the method may comprise electrodepositing a carbon nanotube (CNT) rope (130) on a supporting substrate (110), electrodepositing at least two metal electrodes (140) on the CNT rope (130) disposed on the supporting substrate (110) such that a portion of the CNT rope is disposed in-between the two metal electrodes (140), depositing a photoresist layer (120) on the two metal electrodes (140), CNT rope (130), and the supporting substrate (110), lithographically patterning the photoresist layer (120) to form a window (150) through the photoresist layer (120), thus exposing and isolating a portion of the CNT rope (130) disposed between the two metal electrodes (140), and electrodepositing metal nanoparticles (135) onto the CNT rope (130) exposed and isolated between the two metal electrodes (140), thus forming the $H_2$ sensor (105) comprising a metal NP-decorated CNT rope. In further embodiments, metering devices, such as a source-meter in concert with a multimeter, may be operatively connected to the metal electrodes of the $H_2$ gas sensor (105) for measuring sensor resistance. The sensor resistance may be indicative of $H_2$ gas detection by the $H_2$ gas sensor (105).

In preferred embodiments, the step of electrodepositing the metal NPs employs a pulse electrodeposition process comprising applying about 50-400 voltage pulses, each pulse having an applied potential of about −0.8 V vs. SCE and a pulse duration of about 0.1-0.5 second and being separated by about 1-2 second wait times. Without wishing to limit the invention to a particular theory or mechanism, the pulse electrodeposition process can enable formation of metal NPs (135) having a mean particle diameter of about 4-10 nm, as well as maximizing a density of metal NPs formed on the exposed and isolated CNT rope (130), thus producing an $H_2$ sensor (105) capable of detecting $H_2$ in air at an $H_2$ concentration of at least 10 ppm. In some embodiments, the steps of electrodepositing the carbon and electrodepositing the at least two metal electrodes (140) may be consistent with the procedures previously described herein.

EXAMPLE

The following is an example of practicing the present invention presented for illustrative purposes only, and is not intended to limit the present invention in any way. Equivalents or substitutes are within the scope of the invention.

Dielectrophoretic Deposition of Patterned Single CNT Ropes.

Hydrogen sensors were prepared using a variant of the lithographically patterned nanowire electrodeposition (LPNE) method. Said LPNE method for patterning the electrodes and depositing carbon nanotube ropes is described in U.S. Pat. No. 8,142,984, the specification of which is incorporated herein by reference. Aqueous dispersions of SWNTs used for dielectrophoretic deposition containing 10 mg/L SWCNTs and 0.1 g/L sodium dodecylsulfate (SDS) were first sonicated for 6 hours to disperse the SWCNTs. The procedures of dielectrophoretic deposition of SWNTs was carried out at LPNE-patterned nickel electrodes. The process for preparation of the LPNE templates are summarized in FIG. 1. In step 1, nickel films of 40 nm thickness were thermally evaporated onto pre-cleaned 3 in.×1 in. soda lime glasses, the thickness of nickel films was precisely measured by gold quartz crystal microbalance (QCM). In step 2, a positive photoresist layer was spin-coated at 2500 rmp for 80 seconds, and baked in a forced convection oven at 90° C. for 30 minutes. After the photoresist layer was cooled down to room temperature, it was mounted in contact with quartz mask on photolithographic mask alignment fixture. Then, in step 3, the photoresist layer was patterned by a flood exposure UV light source. The whole region of exposed photoresist was immersed in the photoresist developer for 20 seconds, rinsed with Millipore water, and air dried. In step 4, the sample was dipped in 0.8 M nitric acid for 5-10 minutes in order to etch away exposed nickel and also to produce a horizontal undercut beneath the protective photoresist layer. The height of this undercut equaled the thickness of the nickel evaporated in step 1.

In step 5, the nickel edge within this horizontal trench was used as the working electrode for the dielectrophoretic deposition of SWNTs ropes. A 50 mL one-compartment two-electrode electrochemical cell was used for dielectrophoretic deposition of CNTs. The photolithographically patterned Ni electrode was immersed in aqueous solution of dispersed SWNTs while leaving the other edge of nickel out of the solution and connected to a sourcemeter. The counter electrode was a pre-cleaned 1 $cm^2$ platinum foil. The dielectrophoretic deposition of CNT ropes was accomplished from an aqueous solution containing 10 mg/L SWCNTs and the 0.1 g/L sodium dodecylsulfate (SDS) by the application of a series of voltage pulses having an amplitude of 20V, a duration of 0.1 s, at a rate of one pulse every two seconds. A total of 100 pulses were applied to generate the CNT ropes used in the devices described herein. When the deposition was finished, the remaining photoresist layer was completely dissolved and rinsed off by acetone, and then nickel layer was totally etched away by 0.8 M nitric acid, leaving one single SWNTs bundle adhering strongly to the glass surface. These processes are also comprised in step 5.

As further shown in FIG. 1, subsequent steps were associated with the preparation of electrical contacts and the electrodeposition of Pd nanoparticles. In step 6, a layer of 2 nm Cr was thermally evaporated onto the as-made single SWNTs bundles, followed by the second thermal metal evaporation of 80 nm Au. Then, in step 7, a layer of photoresist was spin-coated and baked as previously described. After the photoresist layer was patterned, in steps 8 and 9, the uncovered part of Au/Cr layers was etched away, leaving patterned metallic layers on both sides of a 50 µm-long single bundle SWNTs.

Figure 2A:
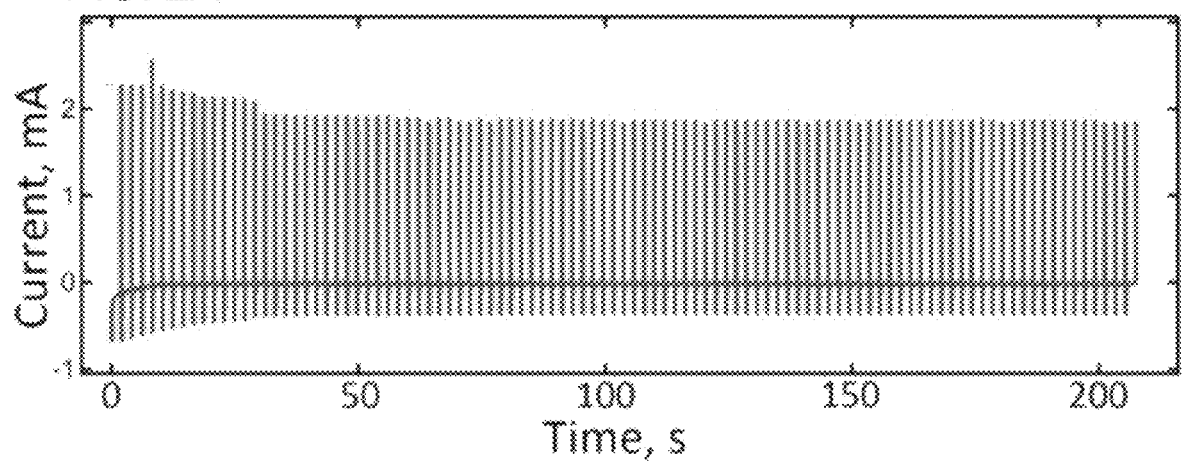
FIGS. 2A-2E show non-limiting examples of Patterning of CNT ropes prepared by LPNE-templated dielectrophoresis.
Figure 2B:
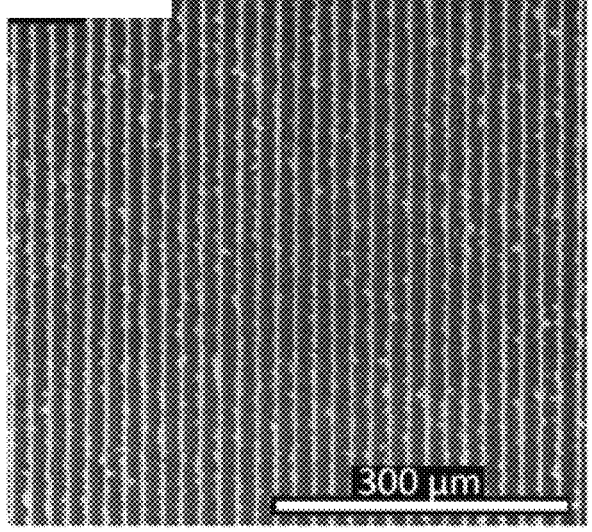
Figure 2C:
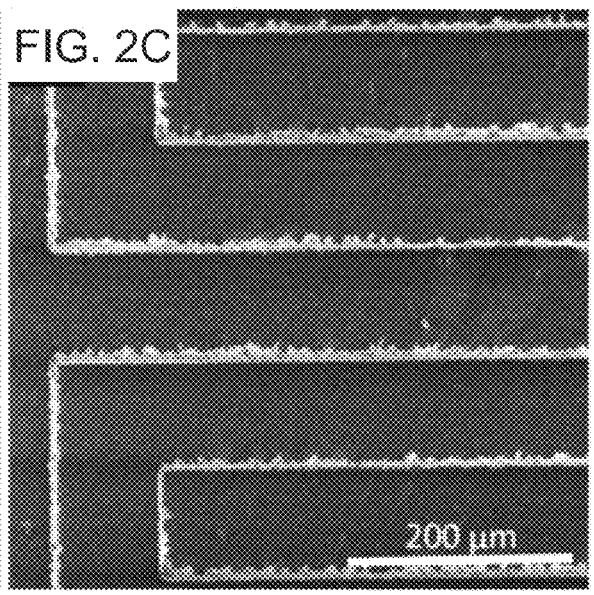
Figure 2D:
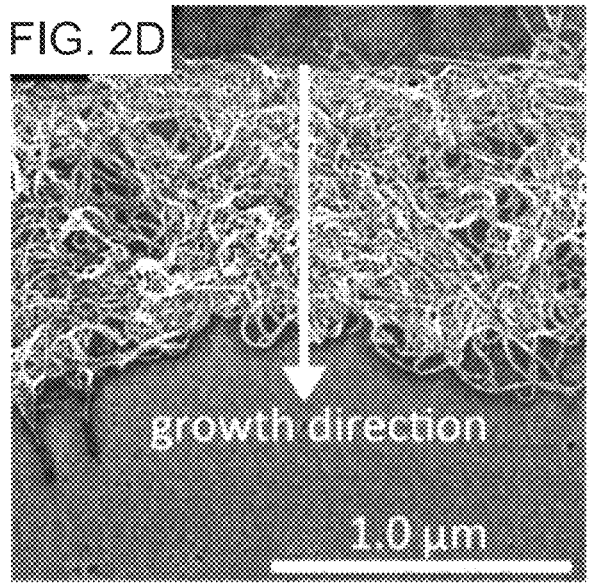
Figure 2E:
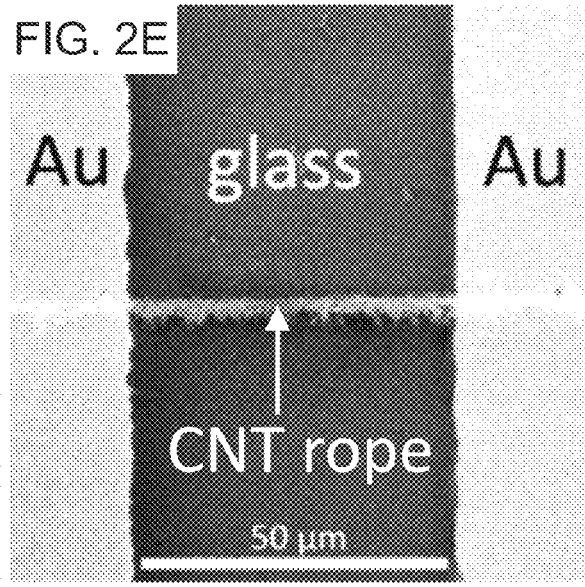

A typical current-time trace acquired during CNT deposition (FIG. 2A) shows an excess of anodic current consistent with the oxidation of water at +20V which occurred concurrently with the deposition of CNTs. The resulting CNT ropes consist of tangled assemblies of CNTs with a mean width of 1-2 µm (FIG. 2D). The rope width dispersion of these CNT ropes is evident from these images. A 50 µm length was electrically isolated using evaporated gold contacts on a 2 nm thickness adhesive chromium interlayer (FIG. 2E).

Alignment of individual CNTs with the axis of the rope was generally obtained because this direction coincides with the direction of the electric field gradient in the system. Without wishing to limit the invention to a particular theory or mechanism, more disordered ropes have been obtained when the electric field gradient driving deposition is oriented orthogonal to the axis of the deposited rope. This is the deposition geometry operating in the present invention for the deposition of CNT ropes using LPNE. In some embodiments, the LPNE patterning of dielectrophoretically deposited CNT ropes can be used to create arrays of linear ropes, as shown in FIG. 2B, or ropes having more complex patterns, as shown in FIG. 2C.

Electrochemical Decoration of Pd Nanoparticles and Fabrication of Hydrogen Gas Sensor.

Referring to steps 10-13 of FIG. 1, Pd nanoparticles were electrodeposited on 50 µm long sections of CNT ropes isolated between the lithographically patterned gold contacts using a three-electrode electrochemical cell with saturated calomel reference electrode (SCE) and a platinum counter electrode. The aqueous plating solution contains 0.2 mM $PdCl_2$, 0.22 mM EDTA and 0.1 M KCl. The Pd nanoparticles were electrodeposited by pulsing applied potential. Both $Pd^{2+}$ reduction and hydrogen evolution can be expected to occur concurrently at this potential, and both are irreversible processes (FIG. 3A). Pd nanoparticles were prepared on CNT ropes in this solution by applying voltage pulses of −0.80 V (vs. SCE), 100 ms separated by 2 s wait times at 0.0 V (FIG. 3B). Without wishing to limit the invention to a particular theory or mechanism, this pulsed deposition scheme may maximize the number density of Pd nanoparticles produced on the CNT rope because each pulse exceeds an overpotential for palladium deposition, $\eta_{Pd}$, while the wait time between pulses allows $Pd^{2+}$ ions to diffusively back-fill into the CNT rope after each pulse. $\eta_{Pd}$ is the additional voltage beyond the Nernst potential for Pd2+ reduction that is required to form $Pd^0$ nuclei on CNT surfaces. Since Pd nanoparticle nucleation is first order in $[Pd^{2+}]$, refreshing the $Pd^{2+}$ can enable the highest possible nucleation rate, resulting in size similar nanoparticles with a diameter that is correlated with the total coulombic loading.

Between 50 and 400 deposition pulses were applied to achieve the range of $Q_{Pd}$ values. Integration of the net cathodic charge yielded $Q_{Pd}$ which included contributions from Pd deposition and $H_2$ evolution. A plot of current and integrated charge versus time (FIG. 3C) shows that cathodic currents exceed anodic currents, and the build-up of the total excess cathodic charge, $Q_{Pd}$, can be tracked as a function of time (FIG. 3D). With successive pulses, the current amplitude also increases somewhat, consistent with the electrocatalysis of both $H_2$ evolution and $Pd^{2+}$ reduction by the Pd NPs. This autocatalysis is also observed in the cyclic voltammograms shown in FIG. 3A that show increasing peak currents on three successive voltammetric scans. Because the Pd2+ reduction current is augmented by $H_2$ evolution, the measured $Q_{Pd}$ provides an upper limit on the actual Pd loading onto the CNT rope. $Q_{Pd}$ values of 15° C. to 102° C. were investigated herein.

Scanning Electron Microscopy (SEM).

Scanning electron micrographs were acquired by using a FEI Magellan 400 XHR system. Energy dispersive spectroscopic (EDS) images were acquired by the same SEM system with an EDS detector. Acceleration voltages of incident electron beams ranged from 1 kV to 5 kV, and probe currents ranged from 1.6 pA to 0.4 nA. All the SEM specimens were mounted on stainless stubs and held by copper clips.

Transmission Electron Microscopy (TEM).

Transmission electron micrographs were acquired by using high resolution mode of a Philip CM-20 system operating at 200 kV acceleration voltage. Carbon nanotubes bundles with Pd nanoparticles were held by 3 mm diameter amorphous carbon-coated copper TEM grids.

Hydrogen Sensing.

CNT@PdNP $H_2$ sensors were mounted in a sealed flow cell equipped with two input ports—one for pre-mixed hydrogen/air, the other for air balance. The resistance of sensors was measured in situ as sensors were exposed to pulses of hydrogen gas at predetermined mixing ratios. Sensor resistance measurement was accomplished using a source-meter in concert with a multimeter. Flow controllers were used to control gas flow rates and to create pre-mixed hydrogen in air at predetermined mixing ratios. A pair of switching valves provided the means for switching between air balance and pre-mixed hydrogen/air pulses. These were controlled using a National Instruments interface in conjunction with a computer. The gas composition, pulse parameters, and data acquisition were programmed and controlled using Labview. All hydrogen sensing experiments were carried out at ambient laboratory temperature (about 20° C.) at a total gas flow rate of 1000 sccm.

Figure 4A:
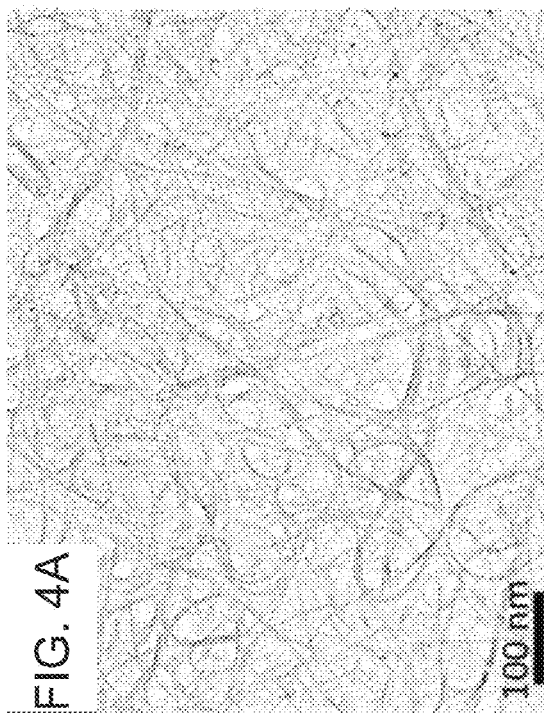
FIGS. 4A-4C show TEM characterization of electrodeposited Pd nanoparticles.
Figure 4B:
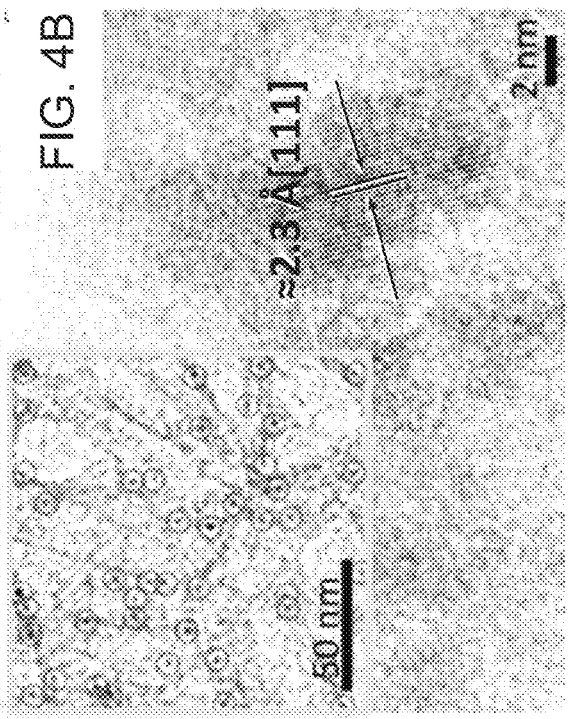
Figure 4C:
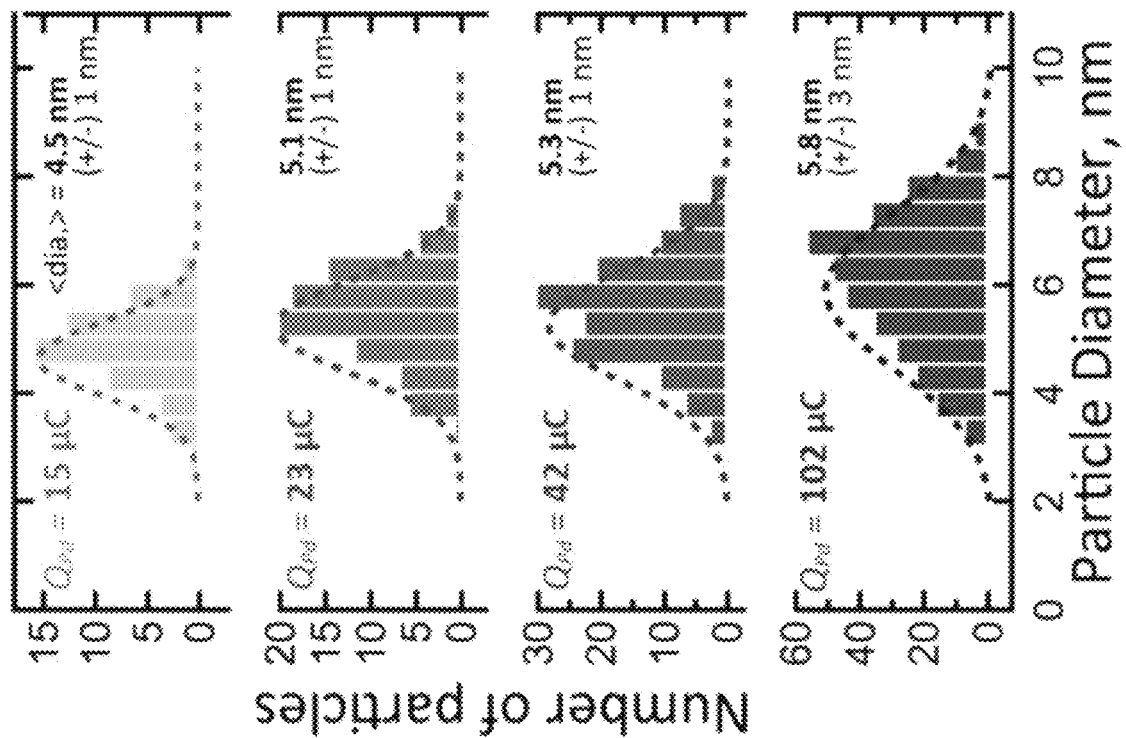

Referring to FIG. 4A, electrodeposited Pd nanoparticles distributed on the CNT sidewalls were characterized using transmission electron microscopy (TEM). Low magnification TEM images show tangles of CNTs within the rope. A few larger Pd NPs can be seen in this image on the lower right hand side, but most of the image appears to show none. However at higher magnification, it is apparent that very small, sub-6 nm diameter Pd NPs are distributed throughout the CNT rope. In the 120 nm×120 nm region shown in yellow in FIG. 4A, for example, about 40 Pd NPs can be located and are highlighted with blue circles in the inset of FIG. 4B. At a still higher magnification of FIG. 4B, an individual Pd NP is revealed at lattice resolution. Using TEM image data, histograms of Pd NPs were compiled as a function of the total deposition charge, $Q_{Pd}$, as shown in FIG. 4C. The mean diameters of Pd NPs ranged from 4.5 (±1) nm for $Q_{Pd}$=15 μC, to 5.8 (±3) nm for $Q_{Pd}$=102 μC. The relative standard deviation of the diameter, $RSD_{dia}$, was in the range from 22% to 52% for these Pd NP distributions (Table 2). Compared with prior research in which Pd has been electrodeposited or vapor deposited onto CNT assemblies (Table 1), the pulsed plating method employed here yielded smaller NPs that are also more narrowly distributed in diameter. Without wishing to limit the invention to a particular theory or mechanism, the enhanced performance of the CNT@PdNP H2 sensors, as described below, may be attributed to the small mean Pd NP diameter, the absence of larger Pd NPs in these distributions, and the cleanliness inherent to the electrodeposition process, which does not require the stabilization of Pd colloids by a ligand layer.

TABLE 1

Performance Metrics for Resistance-Based Hydrogen Sensors Operating in Air.

| Sensing Element[a] | Sensor Type | Sensing Range | $T_{resp}:T_{rec}$[b] (s) | @[$H_2$] (ppm) | $LOD_{H_2}$[c] (ppm) | Ref |
|---|---|---|---|---|---|---|
| Pd@SWCNTs | ChemFET | 200-1000 ppm | 300:500 | 1000 | 200 | 22 |
| Pd@SWCNTs | ChemFET | 25-2000 ppm | 160:500 | 1000 | 25 | 21 |
| Pd@rGO | ChemFET | 1-100 ppm | 50:100 | 50 | 1 | 36 |
| Pd@rGO | Chemiresistor | 20-1000 ppm | 300:1500 | 1000 | 20 | 20 |
| Pt/$SnO_2$@rGO | Chemiresistor | 5000 ppm-3% | 70:40 | 10000 | 5000 | 37 |
| Pd@Carbon nw | Chemiresistor | 10-500 ppm | 200:800 | 500 | 10 | 38 |
| Pd/Ni@SWCNTs | Chemiresistor | 200 ppm-1.6% | 300:500 | 2000 | 200 | 25 |
| Pd/Pt@MWCNTs | Chemiresistor | 400 ppm-4% | 150:200 | 1000 | 400 | 39 |
| Pd@DWCNTs | Chemiresistor | 500 ppm-3% | 180:220 | 1000 | 500 | 40 |
| Pd@SWCNTs | Chemiresistor | 30 ppm-1% | 280:300 | 1000 | 30 | 41 |
| Pd@SWCNTs | Chemiresistor | 100 ppm-2% | 950:3300 | 1000 | 100 | 42 |
| Pt s-nw | Chemiresistor | 10 ppm-4% | 180:1300 | 1000 | 10 | 43 |
| Pd s-nw | Chemiresistor | 500 ppm-4% | 435:445 | 1000 | 500 | 8 |
| Pt@Pd s-nw | Chemiresistor | 500 ppm-4% | 264:120 | 2000 | 500 | 8 |
| Pd@SWCNTs | Chemiresistor | 10 ppm-4% | 62:72 | 1000 | <10 | Present Invention |

[a]Abbreviations: SWCNT = single walled carbon nanotubes, rGO = reduced graphene oxide, nw = nanowire, DWCNT = double walled carbon nanotubes, s-nw = single nanowire.
[b]$T_{resp}$, $T_{rec}$ are response time ($R_{initial}$ to $0.90R_{max}$) and recovery time ($R_{max}$ to $0.10R_{max}$) respectively.
[c]$LOD_H$: Limit-of-detection for hydrogen.

TABLE 2

Parameters for Palladium Nanoparticle-Decorated CNT Rope (Pd-CNT Rope) Hydrogen Sensors.

| $Q_{Pd}{}^a$ (µC) | Number of Sensors | Mean Pd NP dia. (nm) | $R_0{}^b$ (kΩ) | $T_{resp}:T_{rec}{}^c$ (s:s) | $(\Delta R/R_0)_{1000\,ppm}{}^d$ (%) |
|---|---|---|---|---|---|
| 15 (± 1)  | 3 | 4.5 (± 0.8) | 91 | 62:72   | 21 (± 2) |
| 23 (± 1)  | 3 | 5.1 (± 0.9) | 89 | 106:100 | 31 (± 1) |
| 42 (± 1)  | 2 | 5.3 (± 1.3) | 86 | 135:118 | 59 (± 5) |
| 102 (± 3) | 2 | 5.8 (± 2.8) | 80 | 200:182 | 78 (± 2) |

$^a$Total electrodeposition charge for Pd, inclusive of H2 evolution.
$^b$Initial resistance in air.
$^c T_{resp}, T_{rec}$ are response time ($R_0$ to $0.90R_{max}$ where $R_{max}$ is the steady-state resistance measured at 1000 ppm) and recovery time ($R_{max}$ to $0.10R_{max}$), respectively.
$^d$Relative resistance change, $\Delta R/R_0$, observed upon exposure to [$H_2$] = 1000 ppm in air.

Figure 5:
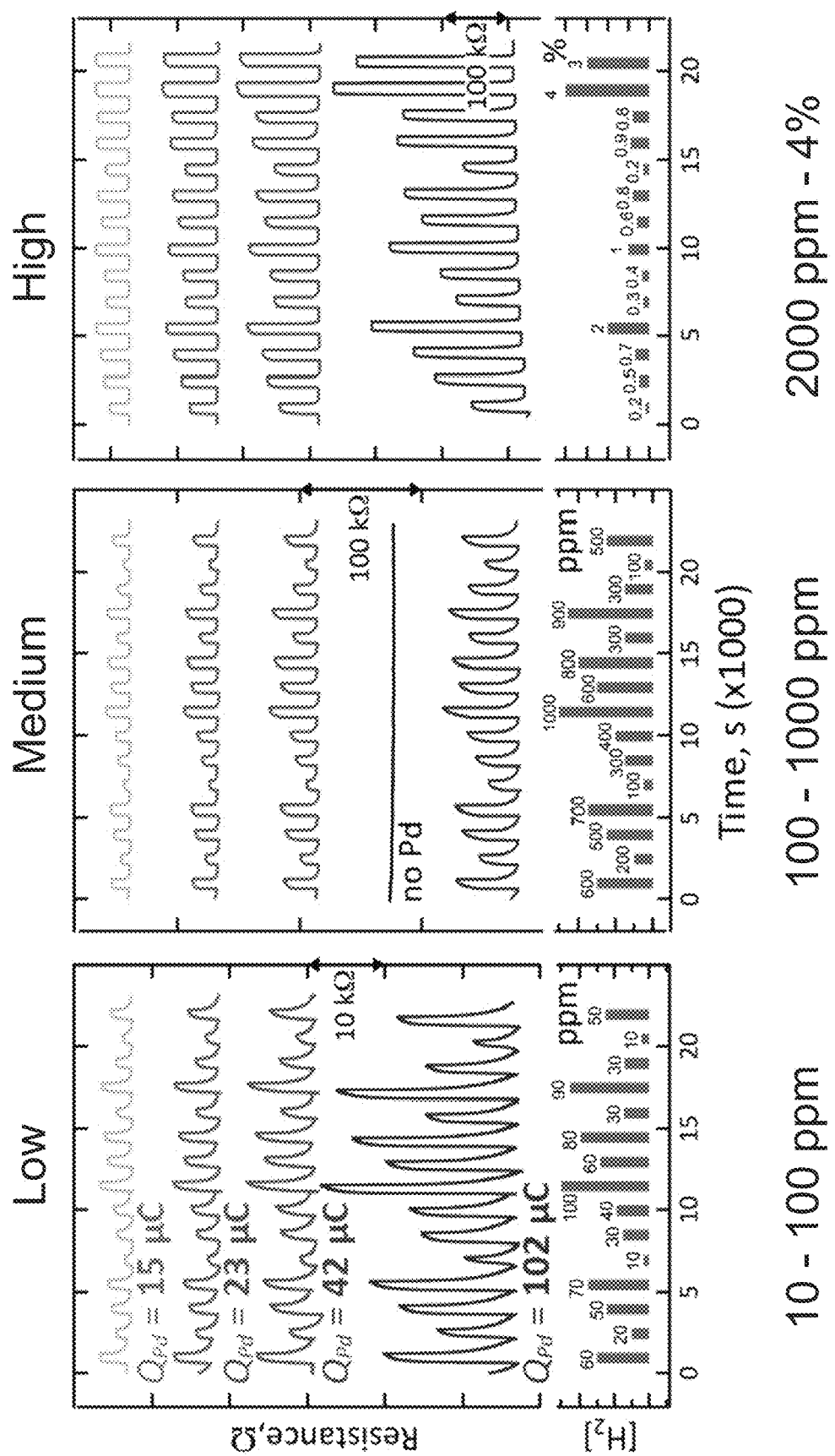
FIG. 5 shows CNT@PdNP $H_2$ sensor responses, for devices prepared using four QPd values, as indicated. $H_2$ densing data for three [$H_2$] concentration ranges, low, medium, and high, are shown: Left, 10 ppm<[$H_2$]<100 ppm; Middle, 100 ppm<[$H_2$]<1000 ppm, Right, 0.2%<[$H_a$]<4%. R0 values, in the 80-90 kΩ range, are provided later in Table 2.
Figure 6A:
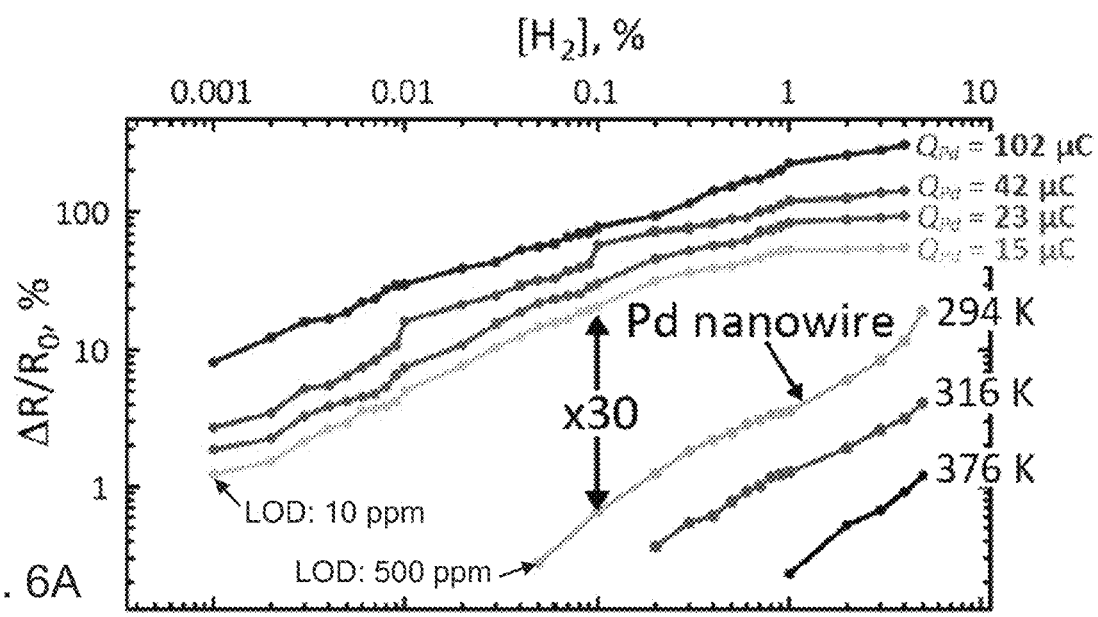
FIGS. 6A-6C show hydrogen sensing metrics for CNT@PdNP $H_2$ sensors, and a comparison to a single Pd nanowire sensor (40 nm×100 nm×50 µm) operated at three temperatures.

Four sets of CNT@PdNP $H_2$ sensors, distinguished based upon the value of $Q_{Pd}$, were tested. These four sensors had $Q_{Pd}$ ranging from 15 µC to 102 µC, corresponding to mean Pd NP diameters of 4.5 nm to 5.8 nm (FIG. 3C). Referring to FIG. 5, the response of each sensor was evaluated across a $H_2$ concentration of 10 ppm to 40,000 ppm (4%) at room temperature in air. CNT ropes that were not decorated with Pd NPs showed no detectable response to $H_2$ at any concentration in this range (c.f. middle panel, black trace). All Pd CNT@PdNP $H_2$ sensors produced a prompt, reversible increase in resistance, $\Delta R$, upon exposure to $H_2$. $\Delta R$ were normalized by the initial resistance, $R_0$, to obtain a dimensionless signal, $\Delta R/R_0$. The amplitude of $\Delta R/R_0$ is striking because it is significantly larger than what is seen for single Pd nanowire sensors, which constitute some of the fastest and most sensitive $H_2$ sensors known so far. A comparison with a Pd nanowire with lateral dimensions of 40 nm×100 nm shown in FIG. 6A reveals, for example, that $\Delta R/R_0$ is 30 times higher for the least sensitive CNT@PdNP ($Q_{Pd}$=15 µC) at 1000 ppm. If the Pd nanowire is heated to accelerate response and recovery to $H_2$ exposure, then the disparity is even larger because the signal amplitude is decreased (FIG. 6A). All four CNT@PdNP $H_2$ sensors were able to detect $H_2$ at 10 ppm with a signal-to-noise of at least 10 (FIG. 5, left panel) while a Pd nanowire produced a $LOD_{H2}$ of 400 ppm with a signal-to-noise ratio of 2.8. Thus, and without wishing to be bound by theory, it may be concluded that the CNT@PdNP $H_2$ sensors were much more sensitive than Pd nanowires, producing significantly lower $LOD_{H2}$ and expanded dynamic range for the detection of [$H_2$]. Sensing metrics and Pd NP statistics are both summarized in Table 2.

Figure 6B:
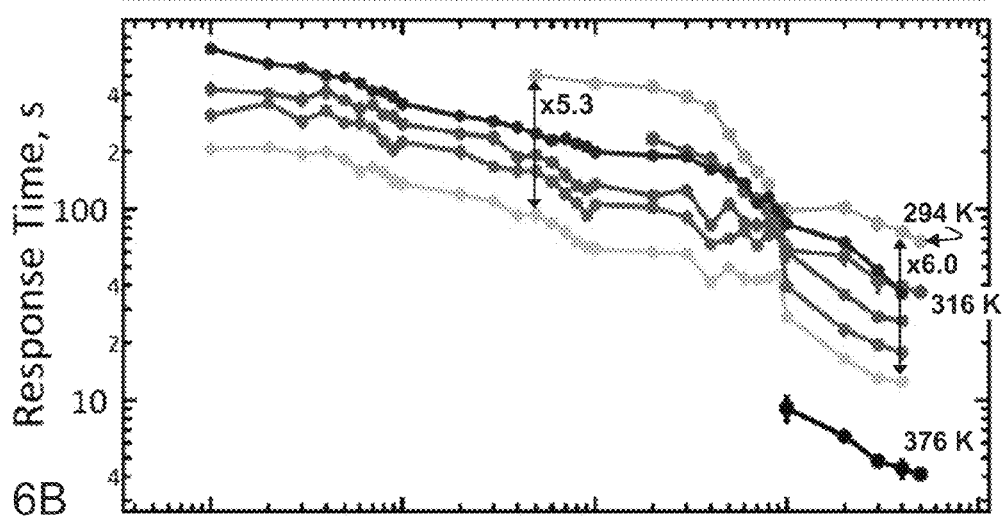
Figure 6C:
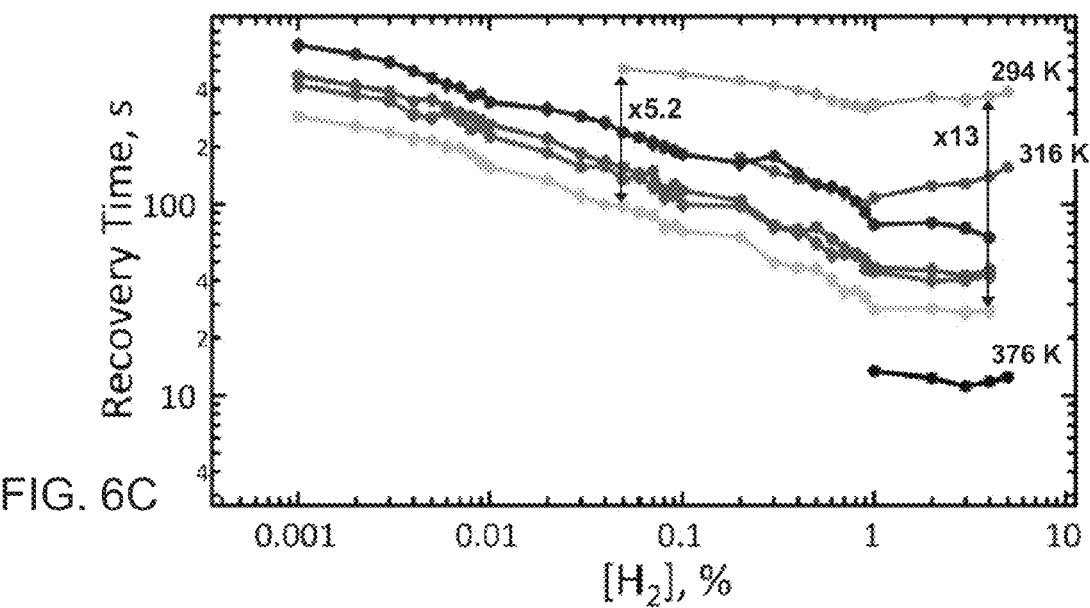
Figure 7A:
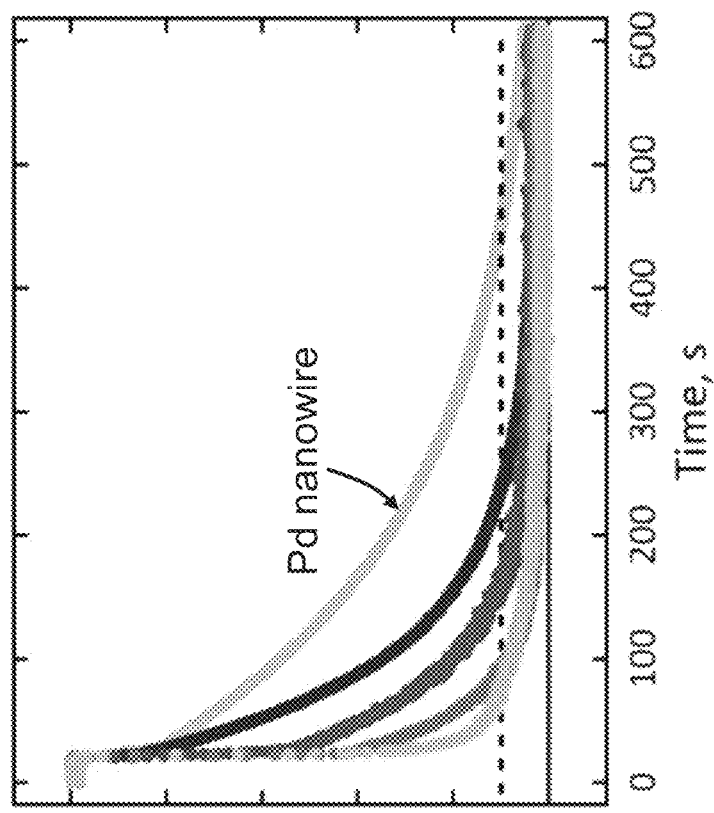
FIGS. 7A-7B are comparisons of response (FIG. 7A) and recovery (FIG. 7B) for a single Pd nanowire $H_2$ sensor (40 nm (h)×100 (w)×50 µm) and CNT@PdNP $H_2$ sensors with QPd values of 15 µC, 23 µC, 42 µC, 102 µC, as indicated. [$H_2$]=1000 ppm. The horizontal dashed line indicates $\Delta R/R_{max}$=0.90.
Figure 7B:
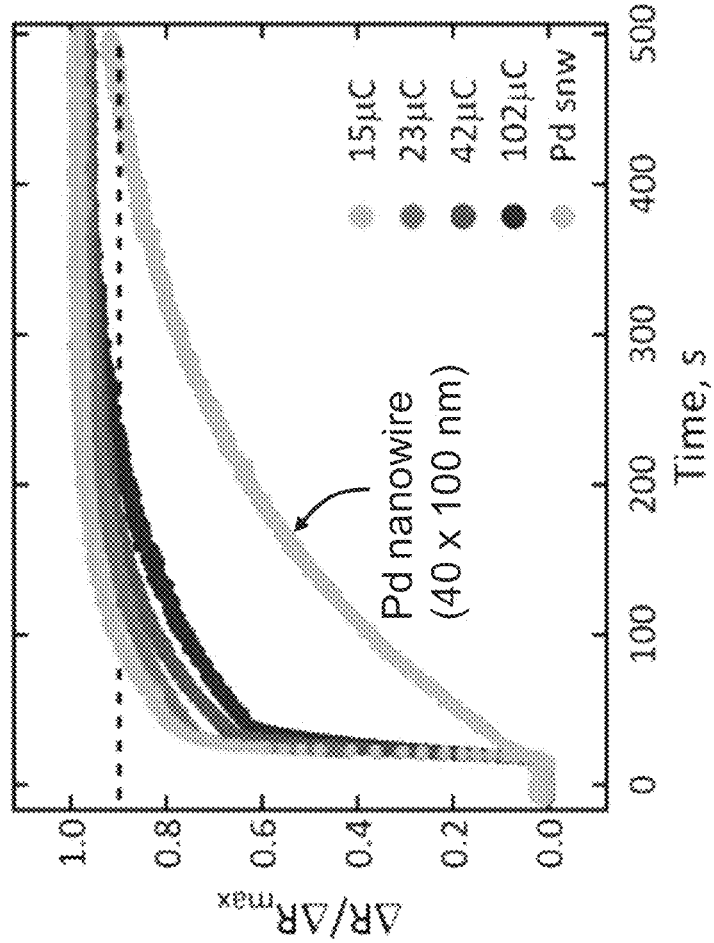

For CNT@PdNP $H_2$ sensors, $Q_{Pd}$ influences sensor performance in two ways: First, the amplitude of the relative resistance change, $\Delta R/R_0$, increases with $Q_{Pd}$. $Q_{Pd}$=102 µC sensors produced $\Delta R/R_0$ values that are 6-8 times as high as those seen for $Q_{Pd}$=15 µC sensors across this entire [$H_2$] range; Second, response and recovery times improve (decrease) with decreasing $Q_{Pd}$ across the concentration range tested (FIG. 6B, 6C). As shown in FIG. 7B, the effect of Pd NP diameter is strongest on recovery. Again, CNT@PdNP $H_2$ sensors are significantly faster than Pd nanowires operating at room temperature. The influence of $Q_{Pd}$ on sensor speed is most evident in the lowest $H_2$ concentrations (FIG. 5, left). For $Q_{Pd}$ of 23 µC, 42 µC, and 102 µC, $\Delta R/R_0$ does not reach a steady-state, time-invariant value on the time scale of the 700 s exposures. A time-invariant response is seen for $Q_{Pd}$=15 µC sensors because of the more rapid response and recovery of $\Delta R/R_0$. Since even $Q_{Pd}$=15 µC CNT@PdNP sensors have an abundance of signal-to-noise and can readily detect 10 ppm, these sensors out-perform the three with larger $Q_{Pd}$ for the detection of $H_2$.

It has been described herein novel $H_2$ sensors operating across a broad dynamic range of 3.5 orders of magnitude and having a limit-of-detection of <10 ppm and the ability to produce analytically useful response and recovery speeds even at $H_2$ concentrations below 100 ppm. The capabilities of the present invention eclipse those of single palladium nanowires operating at any single temperature. It has also been demonstrated the ability to produce CNT@PdNP $H_2$ sensors with reproducible and controllable properties using the processes disclosed herein.

As used herein, the term "about" refers to plus or minus 10% of the referenced number.

The disclosures of the following U.S. patents are incorporated in their entirety by reference herein: U.S. Pat. No. 8,142,984.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

REFERENCES

1. Buttner, W. J.; Post, M. B.; Burgess, R.; Rivkin, C. An Overview of Hydrogen Safety Sensors and Requirements. Int. J. Hydrogen Energy 2011, 36, 2462-2470.
2. Rivkin, C.; Blake, C.; Burgess, R.; Buttner, W. J.; Post, M. B. A National Set of Hydrogen Codes and Standards for the United States. Int. J. Hydrogen Energy 2011, 36, 2736-2741.
3. Hübert, T.; Boon-Brett, L.; Black, G.; Banach, U. Hydrogen Sensors—a Review. Sensor Actuat. B—Chem. 2011, 157, 329-352.
4. Korotcenkov, G.; Han, S. D.; Stetter, J. R. Review of Electrochemical Hydrogen Sensors. Chem. Rev. 2009, 109, 1402-1433.
5. Cheng, P.; Han, P.; Zhao, C.; Zhang, S.; Zhang, X.; Chai, Y. Magnesium Inference Screw Supports Early Graft Incorporation with Inhibition of Graft Degradation in Anterior Cruciate Ligament Reconstruction. Sci. Rep. 2016, 6, 2-12.

6. Windhagen, H.; Radtke, K.; Weizbauer, A.; Diekmann, J.; Noll, Y.; Kreimeyer, U.; Schavan, R.; Stukenborg-Colsman, C.; Waizy, H. Biodegradable Magnesium-based Screw Clinically Equivalent to Titanium Screw in Hallux Valgus Surgery: Short Term Results of the First Prospective, Randomized, Controlled Clinical Pilot Study. Biomed. Eng. Online 2013, 12, 1.
7. Hughes, R. C.; Schubert, W. K. Thin-films of Pd/Ni Alloys for Detetion of High Hydrogen Concentrations. J. Appl. Phys. 1992, 71, 542-544.
8. Li, X. W.; Liu, Y.; Hemminger, J. C.; Penner, R. M. Catalytically Activated Palladium@Platinum Nanowires for Accelerated Hydrogen Gas Detection. ACS Nano 2015, 9, 3215-3225.
9. Yang, F.; Taggart, D.; Penner, R. Joule Heating a Palladium Nanowire Sensor for Accelerated Response and Recovery to Hydrogen Gas. Small 2010, 6, 1422-1429.
10. Yang, F.; Kung, S.-C.; Cheng, M.; Hemminger, J. C.; Penner, R. M. Smaller is Faster and More Sensitive: The Effect of Wire Size on the Detection of Hydrogen by Single Palladium Nanowires. ACS Nano 2010, 4, 5233-5244.
11. Yang, F.; Taggart, D. K.; Penner, R. M. Fast, Sensitive Hydrogen Gas Detection Using Single Palladium Nanowires That Resist Fracture. Nano Lett. 2009, 9, 2177-2182.
12. Zeng, X.; Latimer, M.; Xiao, Z.; Panuganti, S.; Welp, U.; Kwok, W.; Xu, T. Hydrogen Gas Sensing with Networks of Ultrasmall Palladium Nanowires Formed on Filtration Membranes. Nano Lett. 2010, 11, 262-268.
13. Offermans, P.; Tong, H. D.; van Rijn, C. J. M.; Merken, P.; Brongersma, S. H.; Crego-Calama, M. Ultralow-power Hydrogen Sensing with Single Palladium Nanowires. Appl. Phys. Lett. 2009, 94, 223110.
14. Collins, P. G.; Bradley, K.; Ishigami, M.; Zettl, A. Extreme Oxygen Sensitivity of Electronic Properties of Carbon Nanotubes. Science 2000, 287, 1801-1804.
15. Liu, R.; Ding, H.; Lin, J.; Shen, F.; Cui, Z.; Zhang, T. Fabrication of Platinum-decorated Singlewalled Carbon Nanotube Based Hydrogen Sensors by Aerosol Jet Printing. Nanotechnology 2012, 23, 505301.
16. Kumar, M. K.; Ramaprabhu, S. Nanostructured Pt Functionlized Multiwalled Carbon Nanotub Based Hydrogen Sensor. J. Phys. Chem. B 2006, 110, 11291-11298.
17. Kaniyoor, A.; Jafri, R. I.; Arockiadoss, T.; Ramaprabhu, S. Nanostructured Pt Decorated Graphene and Multiwalled Carbon Nanotube Based Room Temperature Hydrogen Gas Sensor. Nanoscale 2009, 1, 382-386.
18. Khalap, V. R.; Sheps, T.; Kane, A. A.; Collins, P. G. Hydrogen Sensing and Sensitivity of Palladium-decorated Single-walled Carbon Nanotubes with Defects. Nano Lett. 2010, 10, 896-901.
19. Wang, J.; Singh, B.; Park, J.-H.; Rathi, S.; Lee, Maeng, S.; Joh, Lee, C.-H.; Kim, G.-H. Dielectrophoresis of Graphene Oxide Nanostructures for Hydrogen Gas Sensor at Room Temperature. Sensor Actuat. B—Chem. 2014, 194, 296-302.
20. Chung, M. G.; Kim, D. H.; Seo, D. K.; Kim, T.; Im, H. U.; Lee, H. M.; Yoo, J. B.; Hong, S. H.; Kang, T. J.; Kim, Y. H. Flexible Hydrogen Sensors Using Graphene with Palladium Nanoparticle Decoration. Sensor Actuat. B—Chem. 2012, 169, 387-392.
21. Zhang, M. L.; Brooks, L. L.; Chartuprayoon, N.; Bosze, W.; Choa, Y. H.; Myung, N. V. Palladium/Single-walled Carbon Nanotube Back-to-back Schottky Contact-based Hydrogen Sensors and Their Sensing Mechanism. ACS Appl. Mater. Interfaces 2014, 6, 319-326.
22. Choi, B.; Lee, D.; Ahn, J. H.; Yoon, J.; Lee, J.; Jeon, M.; Kim, D. M.; Kim, D. H.; Park, I.; Choi, Y. K. et al. Investigation of Optimal Hydrogen Sensing Performance in Semiconducting Carbon Nanotube Network Transistors with Palladium Electrodes. Appl. Phys. Lett. 2015, 107, DOI: 10.1063/1.4935610.
23. Dhall, S.; Jaggi, N.; Nathawat, R. Functionalized Multiwalled Carbon Nanotubes Based Hydrogen Gas Sensor. Sensor Actuat. A-Phys. 2013, 201, 321-327.
24. Lee, J.-H.; Kang, W.-S.; Najeeb, C. K.; Choi, B.-S., Choi, S.-W.; Lee, H. J.; Lee, S. S.; Kim, J.-H. A Hydrogen Gas Sensor Using Single-walled Carbon Nanotube Langmuir-Blodgett Films Decorated with Palladium Nanoparticles. Sensor Actuat. B—Chem. 2013, 188, 169-175.
25. Lin, T. C.; Huang, B. R. Palladium Nanoparticles Modified Carbon Nanotube/Nickel Composite Rods (Pd/CNT/Ni) for Hydrogen Sensing. Sensor Actuat. B—Chem. 2012, 162, 108-113.
26. Pohl, H. A. Theoritical Aspects of Dielectrophoretic Deposition and Separation of Particles. Journal of The Electrochemical Society 1968, 115, 155C-161C.
27. Xiang, C.; Yang, Y.; Penner, R. M. Cheating the Diffraction Limit: Electrodeposited Nanowires Patterned by Photolithography. Chem. Comm. 2009, 859-873.
28. Xiang, C.; Kung, S. C.; Taggart, D.; Yang, F.; Thompson, M. A.; Guell, A. G.; Yang, Y.; Penner, R. M. Lithographically Patterned Nanowire Electrodeposition: A Method for Patterning Electrically Continuous Metal Nanowires on Dielectrics. ACS Nano 2008, 2, 1939-1949.
29. Menke, E. J.; Thompson, M. A.; Xiang, C.; Yang, L. C.; Penner, R. M. Lithographically Patterned Nanowire Electrodeposition. Nat. Mater. 2006, 5, 914-919.
30. Krupke, R.; Hennrich, F.; Weber, H.; Kappes, M.; v. Löhneysen, H. Simultaneous Deposition of Metallic Bundles of Single-walled Carbon Nanotubes Using AC-dielectrophoresis. Nano Lett. 2003, 3, 1019-1023.
31. Suehiro, J.; Zhou, G.; Hara, M. Fabrication of a Carbon Nanotube-based Gas Sensor Using Dielectrophoresis and Its Application for Ammonia Detection by Impedance Spectroscopy. J. Phys. D: Appl. Phys. 2003, 36, L109.
32. Shekhar, S.; Stokes, P.; Khondaker, S. I. Ultrahigh Density Alignment of Carbon Nanotube Arrays by Dielectrophoresis. ACS Nano 2011, 5, 1739-1746.
33. Stokes, P.; Khondaker, S. I. High Quality Solution Processed Carbon Nanotube Transistors Assembled by Dielectrophoresis. Appl. Phys. Lett. 2010, 96, 083110.
34. Monica, A.; Papadakis, S.; Osiander, R.; Paranjape, M. Wafer-level Assembly of Carbon Nanotube Networks Using Dielectrophoresis. Nanotechnology 2008, 19, 085303.
35. Fan, Y.; Goldsmith, B. R.; Collins, P. G. Identifying and Counting Point Defects in Carbon Nanotubes. Nat. Mater. 2005, 4, 906-911.
36. Lee, J. S.; Oh, J.; Jun, J.; Jang, J. Wireless Hydrogen Smart Sensor Based on Pt/Graphene-Immobilized Radio-Frequency Identification Tag. ACS Nano 2015, 9, 7783-7790.
37. Russo, P. A.; Donato, N.; Leonardi, S. G.; Baek, S.; Conte, D. E.; Neri, G.; Pinna, N. Room-Temperature Hydrogen Sensing with Heteronanostructures Based on Reduced Graphene Oxide and Tin Oxide. Angew. Chem. Int. Ed. Engl. 2012, 51, 11053-11057.
38. Lim, Y.; Lee, Y.; Heo, Shin, H. Highly Sensitive Hydrogen Gas Sensor Based on a Suspended Palladium/Carbon Nanowire Fabricated via Batch Microfabrication Processes. Sensor Actuat. B—Chem. 2015, 210, 218-224.

39. Randeniya, L. K.; Martin, P. J.; Bendavid, A. Detection of Hydrogen Using Multi-walled Carbon-nanotube Yarns Coated with Nanocrystalline Pd and Pd/Pt Layered Structures. Carbon 2012, 50, 1786-1792.
40. Rumiche, F.; Wang, H. H.; Indacochea, J. E. Development of a Fast-Response/High-sensitivity Double Wall Carbon Nanotube Nanostructured Hydrogen Sensor. Sensor Actuat. B—Chem. 2012, 163, 97-106.
41. Sun, Y. G.; Wang, H. H. High-performance, Flexible Hydrogen Sensors That Use Carbon Nanotubes Decorated with Palladium Nanoparticles. Adv. Mater. 2007, 19, 2818-2823.
42. Mubeen, S.; Zhang, T.; Yoo, B.; Deshusses, M. A.; Myung, N. V. Palladium Nanoparticles Decorated Single-walled Carbon Nanotube Hydrogen Sensor. J. Phys. Chem. C 2007, 111, 6321-6327.
43. Yang, F.; Donavan, K. C.; Kung, S.-C., Penner, R. M. The Surface Scattering-based Detection of Hydrogen in Air Using a Platinum Nanowire. Nano Lett. 2012, 12, 2924-2930.

What is claimed is:

1. A hydrogen gas ($H_2$) sensor (105) for sensing $H_2$ gas in air, said $H_2$ sensor (105) comprising:
   a. a supporting substrate (110);
   b. a carbon nanotube (CNT) rope (130) electrodeposited onto the supporting substrate (110);
   c. at least two metal electrodes (140) disposed on the CNT rope (130), wherein a portion of the CNT rope (130) is disposed in-between the two metal electrodes (140); and
   d. metal nanoparticles (NPs) (135) electrodeposited onto the portion of the CNT rope (130) that is disposed between the two metal electrodes (140), wherein the metal NPs (135) have a mean particle diameter of about 4-9 nm, wherein said mean particle diameter size enables the $H_2$ sensor (105) to detect $H_2$ in air at an $H_2$ concentration of at least 10 ppm.

2. The sensor of claim 1, wherein the metal NPs (135) comprise palladium, platinum, nickel, gold, or a combination thereof.

3. The sensor of claim 1, wherein the metal electrodes (140) comprise copper, silver, or gold.

4. The sensor of claim 1, wherein the metal electrodes (140) further comprises a chromium adhesive interlayer.

5. A hydrogen gas ($H_2$) sensor (105) for sensing $H_2$ gas in air, said $H_2$ sensor (105) comprising:
   a. a supporting substrate (110);
   b. a carbon nanotube (CNT) rope (130) electrodeposited onto the supporting substrate (110);
   c. at least two metal electrodes (140) electrodeposited on the CNT rope (130), wherein a portion of the CNT rope (130) is disposed in-between the two metal electrodes (140); and
   d. a photoresist layer (120) deposited on the two metal electrodes (140), CNT rope (130), and the supporting substrate (110);
   e. a window (150) formed through the photoresist layer (120) by lithographical patterning, wherein the window (150) exposes and isolates a portion of the CNT rope (130) disposed between the two metal electrodes (140); and
   metal nanoparticles (NPs) (135) electrodeposited onto the portion of the CNT rope (130) that is disposed between the two metal electrodes (140), wherein the metal NPs (135) have a mean particle diameter of about 4-10 nm, wherein said mean particle diameter size enables the $H_2$ sensor (105) to detect $H_2$ in air at an $H_2$ concentration of at least 10 ppm.

6. A hydrogen gas ($H_2$) sensor (105) for sensing $H_2$ gas in air, said $H_2$ sensor (105) comprising:
   a. a supporting substrate (110);
   b. a carbon nanotube (CNT) rope (130) electrodeposited onto the supporting substrate (110);
   c. at least two metal electrodes (140) electrodeposited on the CNT rope (130), wherein a portion of the CNT rope (130) is disposed in-between the two metal electrodes (140); and
   d. a photoresist layer (120) deposited on the two metal electrodes (140), CNT rope (130), and the supporting substrate (110);
   e. a window (150) formed through the photoresist layer (120) by lithographical patterning, wherein the window (150) exposes and isolates a portion of the CNT rope (130) disposed between the two metal electrodes (140); and
   palladium nanoparticles (135) electrodeposited onto the portion of the CNT rope (130) that is exposed and isolated, wherein said electrodepositing the palladium nanoparticles (135) utilizes a pulse electrodeposition process comprising applying about 50-400 voltage pulses, each pulse having an applied potential of about −0.8 V vs. saturated calomel electrode (SCE) and a pulse duration of about 0.1-0.5 second and being separated by about 1-2 second wait times, wherein said pulse electrodeposition process enables formation of the palladium nanoparticles (135) having a mean particle diameter of about 4-10 nm, and maximizes a density of the palladium nanoparticles (135) formed on the exposed and isolated portion of the CNT rope (130), thus producing an $H_2$ sensor (105) capable of detecting $H_2$ in air at an $H_2$ concentration of at least 10 ppm.

* * * * *